US008160719B2

(12) United States Patent
Swoyer et al.

(10) Patent No.: US 8,160,719 B2
(45) Date of Patent: Apr. 17, 2012

(54) BRAIDED ELECTRICAL LEAD

(75) Inventors: John M. Swoyer, Andover, MN (US);
Richard M. Farrell, Grant, MN (US);
Brian K. Farrell, White Bear Lake, MN (US)

(73) Assignee: Greatbatch Ltd., Clarence, NY (US)

( * ) Notice: Subject to any disclaimer, the term of this patent is extended or adjusted under 35 U.S.C. 154(b) by 578 days.

(21) Appl. No.: 11/959,730

(22) Filed: Dec. 19, 2007

(65) Prior Publication Data

US 2008/0147155 A1 Jun. 19, 2008

Related U.S. Application Data

(60) Provisional application No. 60/870,782, filed on Dec. 19, 2006.

(51) Int. Cl.
*A61N 1/372* (2006.01)
(52) U.S. Cl. ........................................................ 607/116
(58) Field of Classification Search ................... 607/116
See application file for complete search history.

(56) References Cited

U.S. PATENT DOCUMENTS

| 3,760,812 | A | 9/1973 | Timm et al. |
| 5,014,721 | A | 5/1991 | Hirschberg |
| 5,057,092 | A | 10/1991 | Webster, Jr. |
| 5,483,022 | A | 1/1996 | Mar |
| 5,683,444 | A | 11/1997 | Huntley et al. |
| 6,213,995 | B1 | 4/2001 | Steen et al. |
| 6,216,045 | B1 | 4/2001 | Black et al. |
| 6,606,522 | B2 | 8/2003 | Schell |
| 6,701,191 | B2 | 3/2004 | Schell |
| 6,721,604 | B1 | 4/2004 | Robinson et al. |
| 6,981,314 | B2 | 1/2006 | Black et al. |
| 7,481,808 | B2 * | 1/2009 | Koyfman et al. ............... 606/41 |
| 7,761,170 | B2 * | 7/2010 | Kaplan et al. ................. 607/116 |
| 2004/0215305 | A1 | 10/2004 | Sage |
| 2005/0021119 | A1 | 1/2005 | Sage et al. |
| 2005/0137665 | A1 * | 6/2005 | Cole ............................. 607/116 |
| 2005/0256521 | A1 * | 11/2005 | Kozel ............................. 606/41 |
| 2006/0106444 | A1 * | 5/2006 | Michael et al. ............... 607/122 |

FOREIGN PATENT DOCUMENTS

| EP | 0732117 | 9/1996 |
| GB | 471122 | 8/1937 |

OTHER PUBLICATIONS

European Search Report, Feb. 21, 2008, Munich, DE.

* cited by examiner

*Primary Examiner* — Michael Kahelin
(74) *Attorney, Agent, or Firm* — Michael F. Scalise

(57) ABSTRACT

An implantable electrical lead having a plurality of insulated conductor strands and a plurality of non-conductor strands braided together to maintain the spacing of the conductors from each other to prevent the crossing of the insulated conductor strands. The non-conductor strands are often polymeric strands. In some leads, the conductor strands and non-conductor strands are braided in opposite clockwise directions from each other. The conductor strands may travel adjacent each other in a clockwise direction, crossing non-conductors alternately over then under, with the immediately adjacent conductor strand doing the same but being out of phase. A diamond braid pattern is used in some embodiments. Braids may be formed over a removable mandrel, or a non-removable shaft or tube. Braiding can provide a structure which maintains its configuration after removal from a mandrel without requiring undue stress application to the strands.

26 Claims, 7 Drawing Sheets he present application claims priority from U.S. Provisional Patent Application Ser. No. 60/870,782, filed Dec. 19, 2006.

BACKGROUND OF THE INVENTION

1. Field of the Invention

The present invention is related generally to medical electrical leads. More specifically, the present invention is related to implantable electrical leads. The present invention may find use in implantable neurological devices, cardiac devices, as well as many other devices.

2. Prior Art

Implantable leads having externally exposed ring or band electrodes can be used to deliver electrical stimulation to surrounding tissue and/or to sense electrical energy produced by the surrounding tissue. Such leads are often implanted, for example, within the epidural or intrathecal spaces of the spinal column, along peripheral nerves, within the brain, and about the heart. Electrical stimulation of the spinal cord has been shown to be effective in relieving intractable pain in some patients. Such electrical stimulation can reduce or eliminate the use of pain relieving drugs. Examples of some leads may be found in U.S. Pat. Nos. 6,721,604; 6,981,314; 6,216,045; and 5,483,022, herein incorporated by reference.

One such lead is formed of polymeric material, for example, polyurethane or silicone. The lead can be nominally 1 mm in outer diameter and about 20 cm in length. A typical lead may have a series of electrodes formed as bands or rings disposed in a spaced apart relationship in a lead distal region. The distal region of the lead can be introduced, for example, into the epidural region for use in stimulation of the spinal column. The lead proximal region may have a corresponding set of band or ring connectors or terminals, one for each corresponding electrode in the distal region. Each proximal region terminal can thus be connected to one distal electrode in a typical configuration.

The terminals can be used to couple the proximal end of the lead to a lead extension, which can in turn be coupled to an implantable pulse generator (IPG). The lead extension can provide added length to extend the reach of the lead to a more distantly placed IPG. In some embodiments, the lead extension is between about 20 and 50 cm in length.

The lead typically has a lumen extending from the proximal end through to the distal region, with the lumen being dimensioned to accept a stiffening member or stylet. The lead, commonly formed of a polymeric material and being very small in cross section, is typically very floppy and not pushable. With a stylet or stiffening member inserted, the lead gains the needed pushability, and can be advanced into and up the spinal column to the desired location.

Small size, in particular, small outer diameter, is desirable for nerve stimulation leads. A small profile is less intrusive and may be easier to deliver. Some peripheral nerve stimulation therapies would benefit from small profile leads. Flexibility is desirable for both ease in delivery and for a more comfortable patient experience, as the patient may be aware of a stiffer implanted lead. A long flex life, the ability to survive a large number of lead flexures over the expected lead lifetime, is also desirable. Some cardiac leads are subjected to flexure with every heart beat. Peripheral nerve stimulation leads may be flexed and twisted with the patient's movements.

Some leads have multiple, electrically independent electrical conductors. Spinal cord stimulation leads include several, often eight, conductors. The conductors are often not arranged haphazardly. A straight or coiled cable of conductors is often used. Issues arise that relate to the orientation and spacing of the conductors as they tend to float inside the lead body tubing. As the conductors float and potentially cross each other, flex life can be negatively impacted.

Different configurations have different benefits and different draw backs. Using straight conductors is not optimal, as they break. The smaller the size, generally, the better the conductor flex life. Also, it is hard to make a coil out of a cable, as there is need to put a great deal of stress on the cable as it is wound around a mandrel in order to make the coil stay after the mandrel is removed. One common conductor uses a 7×7 conductor having seven wires, each having seven filars in a twisted rope-like configuration.

What would be desirable is an arrangement for multiple conductors in a lead that provides for a long flex life and minimizes the float and potential crossing of multiple conductors.

SUMMARY OF THE INVENTION

The present invention provides an elongate implantable medical lead body including a plurality of insulated conductor strands and a plurality of at least N polymer strands, where N is at least two, and in which the insulated conductor strands and polymer strands are braided together to form an elongate braided structure. In some lead bodies, the N insulated conductors are helically wound in a first clockwise direction and the N polymer strands are helically wound in a second clockwise direction opposite to the first direction. Some elongate lead bodies have an outer diameter of less than about 4 mm, the insulated conductors have an outer diameter of less than about ¼ mm, and the lead body has a length from about 5 cm to about 150 cm.

The present invention also provides an implantable electrical lead including a plurality of insulated electrical conductor strands braided with a plurality of non-conductor strands such that the insulated conductors do not directly cross each other. In some leads, the non-conductor strands are polymeric strands. There are at least four non-conductor strands and at least four conductor strands in some lead embodiments. The strands can be braided in diamond patterns, herringbone patterns, and in patterns having two or more adjacent conductors in phase with each other. Some leads have substantially longitudinal or zero degree conductor strands weaving in and out of the non-conductor or polymeric strands.

The present invention further provides an implantable lead including an elongate lead body having a proximal region, a distal region, and an intermediate region disposed between the proximal and distal regions. The lead can also have a sidewall with at least two insulated conductors disposed within the lead body, the insulated conductors extending from the proximal region to the distal region. At least two proximal contacts may be disposed in the lead body proximal region and in electrical contact with the respective at least two insulated conductors, and at least two distal contacts may be disposed in the lead body distal region and in electrical contact with the respective at least two insulated conductors. The insulated conductors may be braided with at least two non-conductive strands such that the insulated conductors do not cross each other. In some leads, the at least two proximal contacts comprise a plurality of proximal contacts and the at least two distal contacts comprise a plurality of distal contacts. The conductor strands and non-conductor strands are braided in opposite clock-wise directions from each other in some embodiments.

These and other objects of the present invention will become increasingly more apparent to those skilled in the art by a reading of the following detailed description in conjunction with the appended drawings.

DETAILED DESCRIPTION OF THE PREFERRED EMBODIMENTS

Figure 1:
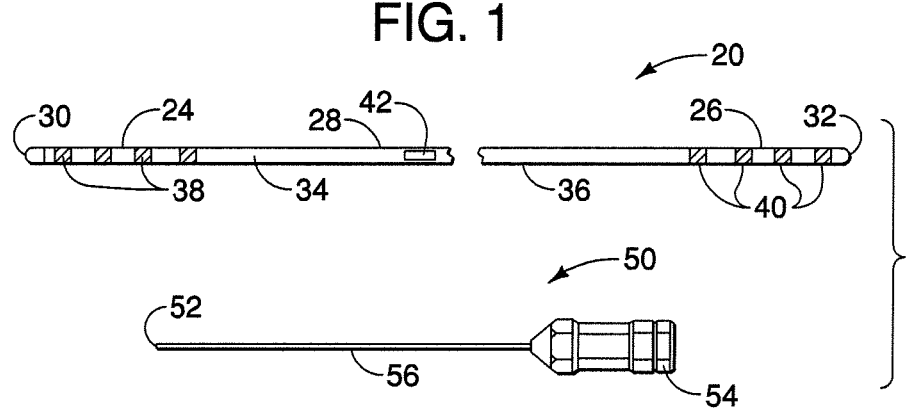
FIG. 1 is a side view of an implantable neurological lead.

FIG. 1 illustrates a neurological stimulation lead 20, similar is some aspects, to the lead illustrated in U.S. Patent Application Pub. No. 2005/0021119, herein incorporated by reference. Lead 20 can incorporate a multi-conductor cable according to the present invention. Lead 20 has a distal region 24, a proximal region 26, and an intermediate region 28 disposed between the distal and proximal regions. In a preferred embodiment, the intermediate region is between the innermost distal and proximal electrical contacts described below. A stylet entrance or insertion port 42 is provided in the intermediate region 28. In other embodiments, the stylet entrance may be absent or lie in the proximal end. Lead 20 can be formed of a body or shaft 34 extending between a distal end 30 and a proximal end 32. Lead body 34 has an exterior surface or tubular side wall 36 and is preferably formed of a polymeric material, for example, polyurethane or silicone.

Lead distal region 24 may include a number of electrodes 38, which, for example, may be disposed concentrically about lead body 34 in a spaced-apart configuration. Electrodes 38 may also be described as electrical contacts or contacts. Electrodes 38 are normally adapted to be inserted into the human body and since they are externally exposed, can be used for neurological stimulation. One exemplary use of electrodes 38 is the stimulation of nerves within the spinal cord. The proximal region 26 can include a number of externally exposed connector bands or connector rings 40 disposed in a spaced-apart configuration to serve as electrical contacts or terminals.

Electrodes 38 and connectors 40 may be formed of platinum and/or iridium. The connectors 40 are used for connecting the lead 20 to a lead extension to extend the effective length of the lead or they may directly couple lead 22 to an implantable pulse generator.

Electrodes 38 and connectors 40 can be coupled to each other in a one-to-one arrangement. In some leads, the distal-most electrode is coupled to the distal-most connector, the second-to-distal-most electrode is coupled to the second-to-distal-most connector, and so forth. The electrodes and connectors can be coupled through conductors extending between them. In some leads, the conductors are embedded within the lead while in other leads, the conductors lie within lumens extending the length of the lead. FIG. 1 also illustrates a stylet 50 that includes a shaft 56 extending between a distal tip 52 and a proximal end or handle 54. The stylet 50 is typically dimensioned to be slidably received within the stylet entrance 42 and a lumen extending distally toward distal region 24.

The lead 20 can be varied in outer diameter and length to suit the application for which it is intended. In some embodiments, the lead 20 has a total length of from about 5 cm and about 150 cm. In other embodiments, the lead 20 has an outer diameter of less than about 1 mm and a total length of from about 10 cm and 150 cm. The lead length between stylet entrance 42 and distal end 30 can vary as well. In some embodiments, the distance from stylet entrance 42 to the distal end 30 is less than 50 cm, preferably less than 30 cm, and most preferably less than about 20 cm. The stylet 50 preferably has a length adapted to approximately match the length between stylet entrance 42 and the distal end 30. The stylet 50 preferably has a shaft outer diameter of less than about 0.050 inches, more preferably less than about 0.020 inches, and most preferably less than about 0.010 inches.

Figure 2:
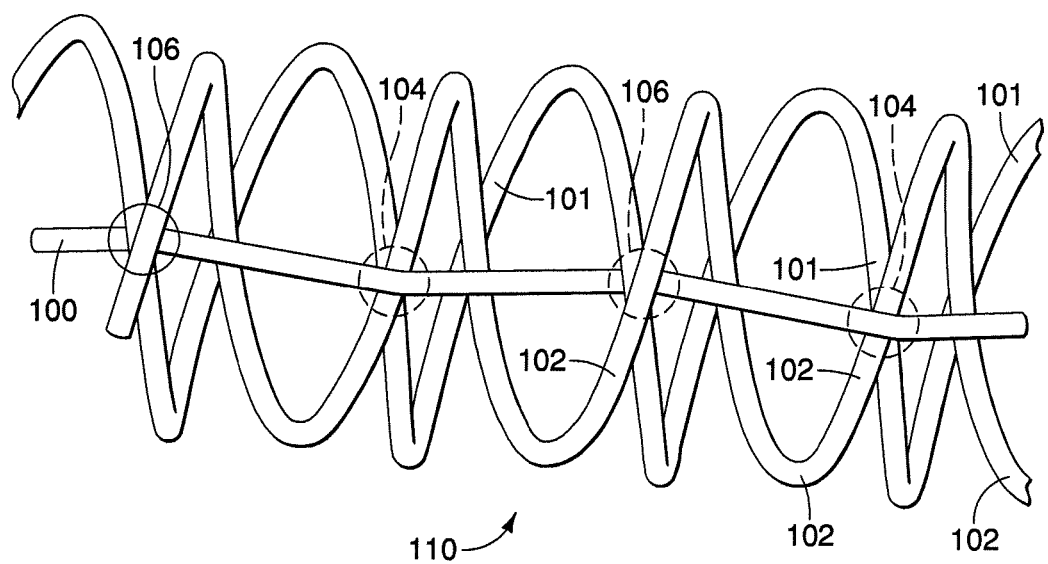
FIG. 2 is a perspective view of one embodiment of the present invention having a two strand polymer braid and a single "linear wave" conductor alternately weaving over and under crossing polymer strand pairs.

FIG. 2 illustrates one embodiment of the invention in a multi-strand cable 110 including an insulated conductor strand 100, a first polymer strand 101, and a second polymer strand 102. In the illustrated embodiment, the first polymer strand 101 is under (inside of) the second polymer strand 102 in front and over (outside of) the second strand 102 in back. The two polymer strands 101, 102 cross in front and in back, with the in-front crossings indicated by reference numerals 104 and 106. As used herein, the term "strand" refers to the elongate members which are braided (can be used to form a braid), and which may be a cable, a bundle, a twisted cable or bundle, a filar or group of filars, etc. Insulated conductor 100 is oriented substantially longitudinally with the longitudinal axis of the multi-strand cable 110, and passing alternatively under and over the polymer crossing regions 104 and 106. In this example, insulated conductor 100 passes over crossing regions 104 and under cross regions 106. In this way, a longitudinal or linear "wave" is imparted to the insulated conductor 100. This provides an increased flex life to the insulated conductor. Conductor strand 100 may be referred to as a zero degree, warp or triaxial, fiber or strand.

In a variation of the embodiment of FIG. 2, the two polymer strands 101, 102 are braided differently. In other embodiments, multiple conductors are included by modifying the braid pattern. In one such embodiment, another such zero degree conductor is woven in and out of the braided polymer strands. The woven braid may be inserted in a lead body tubing.

Figure 3:
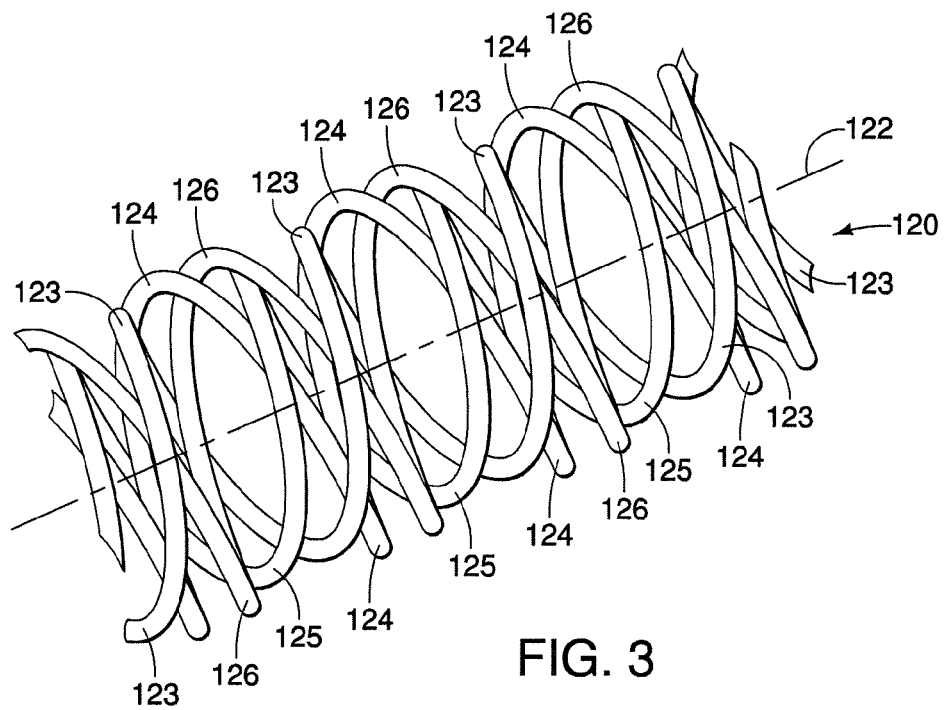
FIG. 3 is a perspective view of another embodiment of the invention having two poly strands braided with two conductor strands.

FIG. 3 illustrates another multi-strand cable 120 having a central longitudinal axis 122, a first insulated conductor 123, a second insulated conductor 125, a first polymer strand 124, and a second polymer strand 126. The first conductor strand 123 and the second conductor strand 125 do not directly cross each other and each has a substantially coiled shape. This forms an essentially coiled structure within the braid which imparts increased flex life to the conductors. In this embodiment, the braided polymer strands maintain the overall configuration.

The multi-strand cable 120 represents a 2×2 diamond braid, where the insulated conductors 123, 125 are wound in a first direction (e.g. clockwise) and the polymer strands 124, 126 are wound in a second, opposite direction (i.e. counterclockwise). This 2×2 diamond braid, as well as 1×1, 3×3, 4×4, 8×8, etc diamond braids are explicitly within the scope of the invention. The conductors 123, 125 run side by side, so they do not cross other conductors, but only polymer strands 124, 126. In this way, the conductors 123, 125 do not rub up against each other, which could lead to a short. Since the braid maintains this configuration, not as much stress must be placed on the conductors 123, 125 in order to maintain them in the desired shape.

Figure 4A:
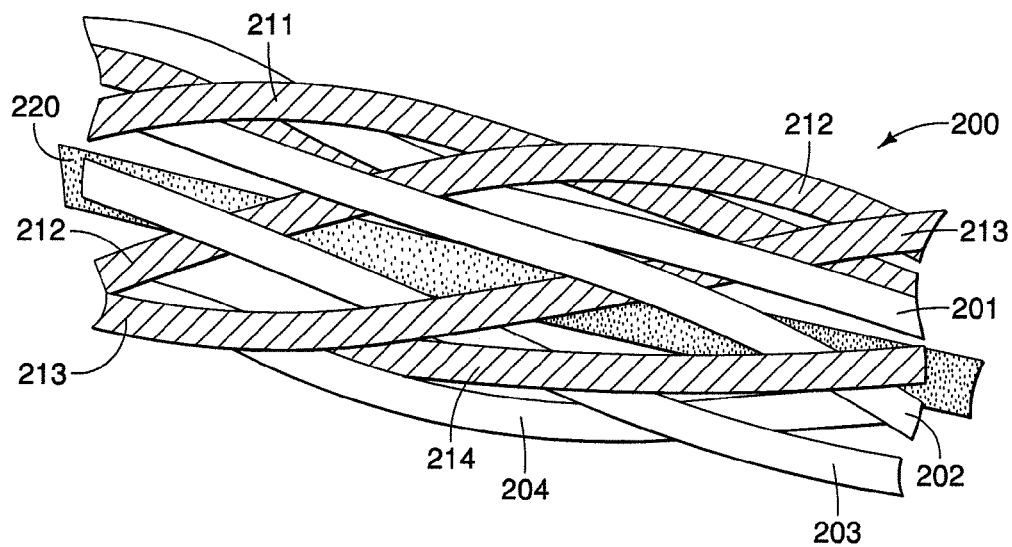
FIG. 4A is a perspective view of an embodiment of the invention having four polymer strands braided with four conductor strands.
Figure 4B:
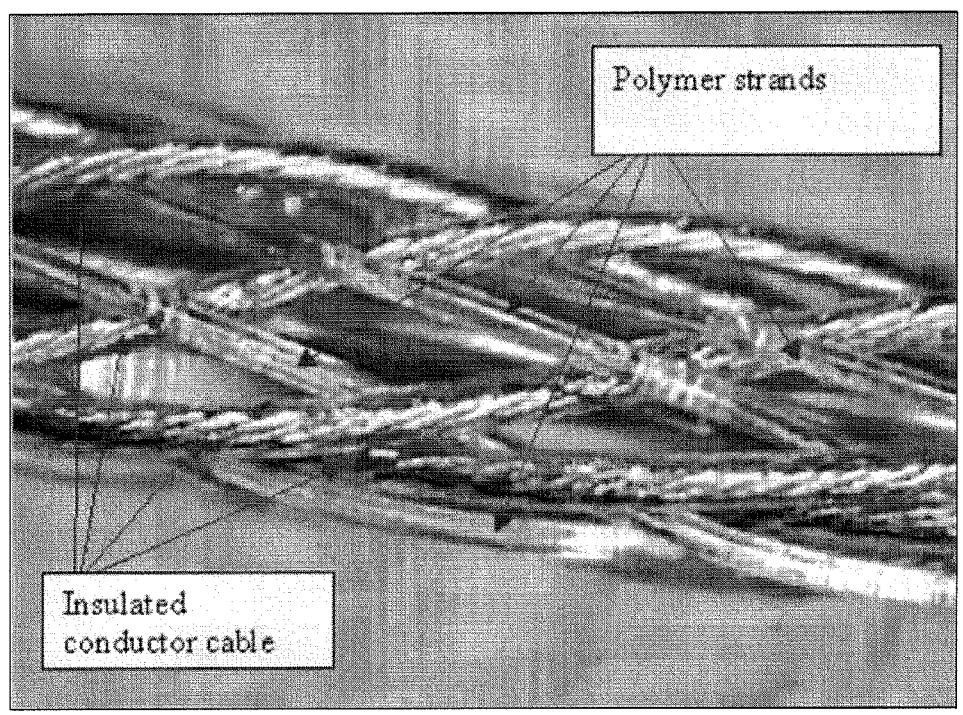
FIG. 4B is a photograph of the embodiment of FIG. 4A.

FIG. 4A is an illustration of another embodiment of a multi-strand cable 200 according to the invention. FIG. 4B is a photograph of embodiment 200. The cable 200 is formed around a mandrel 220 running along the central longitudinal axis thereof. The cable 200 includes a first insulated conductor strand 211, a second insulated conductor strand 212, a third insulated conductor strand 213, and fourth insulated conductor strand 214. The insulated conductor strands 211, 212, 213 and 214 are each formed of seven twisted wires, each wire being formed of seven twisted filaments of a metallic construction. The filaments are made of stainless steel, but could be any metal or metal alloy, including platinum, platinum/iridium, MP35N, silver cored MP35N, etc. The insulated conductors have a polymer outer layer, for example an ETFE or other fluoropolymer coating. Any insulative material suitable for long term implant, including, PTFE, ETFE, polyimide, PEEK, polyurethane, silicone, etc., may be used. The cable 200 also includes a first polymer strand 201, a second polymer strand 202, a third polymer strand 203, and a fourth polymer strand 204.

Inspection of FIG. 4A shows that going from right to left, the first and second polymer strands 201 and 202 are adjacent to each other. The polymer strands 201 and 202 both cross over the first conductor encountered (third conductor strand 213), then the first polymer strand 201 crosses under the next conductor encountered (the second conductor 212) with the second polymer strand 202 also crossing under the same conductor in the same region, then both polymer strands 201 and 202 cross under the next conductor encountered, then (not visible in FIG. 4A) the first polymer strand 201 and the second polymer strand 202 both cross over the next conductor.

Similarly, following a pair of adjacent conductors 212 and 213 from right to left shows that the second conductor 212 crosses over the polymer strand 201 while the third conductor strand 213 crosses under, then both the second and third conductor strands 212 and 213 cross under the next polymer strand 202, then the second conductor strand 212 crosses under the next polymer strand 203 while the third conductor strand 213 crosses over. This pattern may be termed a herringbone, regular braid pattern, with each polymer strand passing under two conductors, then over two conductors.

Figure 5:
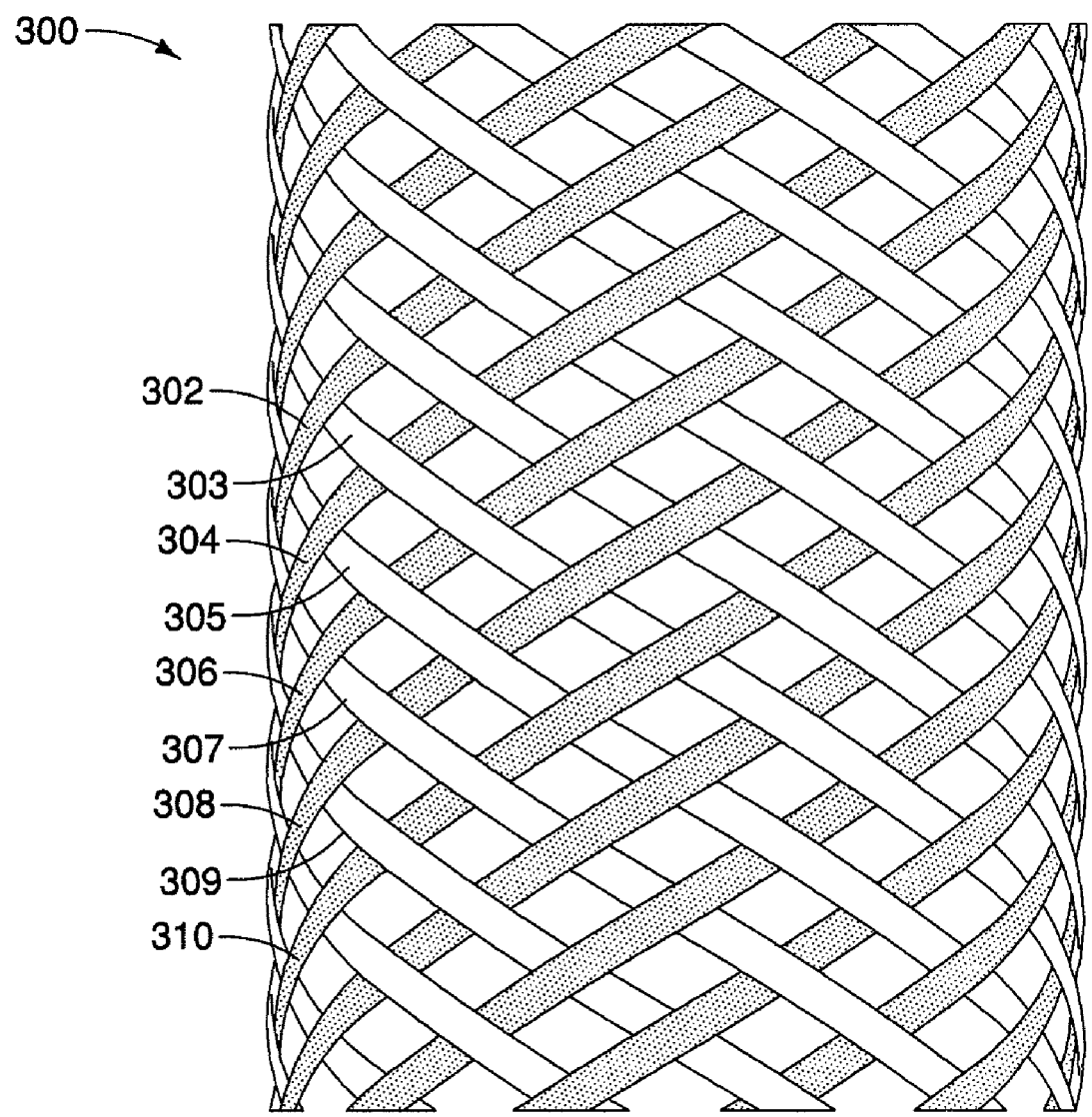
FIG. 5 is a perspective view of a regular braid pattern in which a conductor goes over two polymeric strands then under two polymeric strands.

FIG. 5 illustrates a braid pattern 300 called a herringbone, regular braid pattern, in which one conductor strand passes under two polymeric strands then over two polymeric strands. Five conductor strands 302, 304, 306, 308 and 310 pass from the lower left to the upper right while four polymeric strands 303, 305, 307 and 309 pass from the lower right to the upper left. A conductor strand thus can pass through four different phases which repeat every four strands traveling from side to side, and from conductor to conductor. Conductor strand 302 and strand 310 are in the same phase with respect to the same polymeric strand, for example, strand 303. In this embodiment, there is the same number of conductor and polymeric strands wrapped helically about the center axis.

Figure 6:
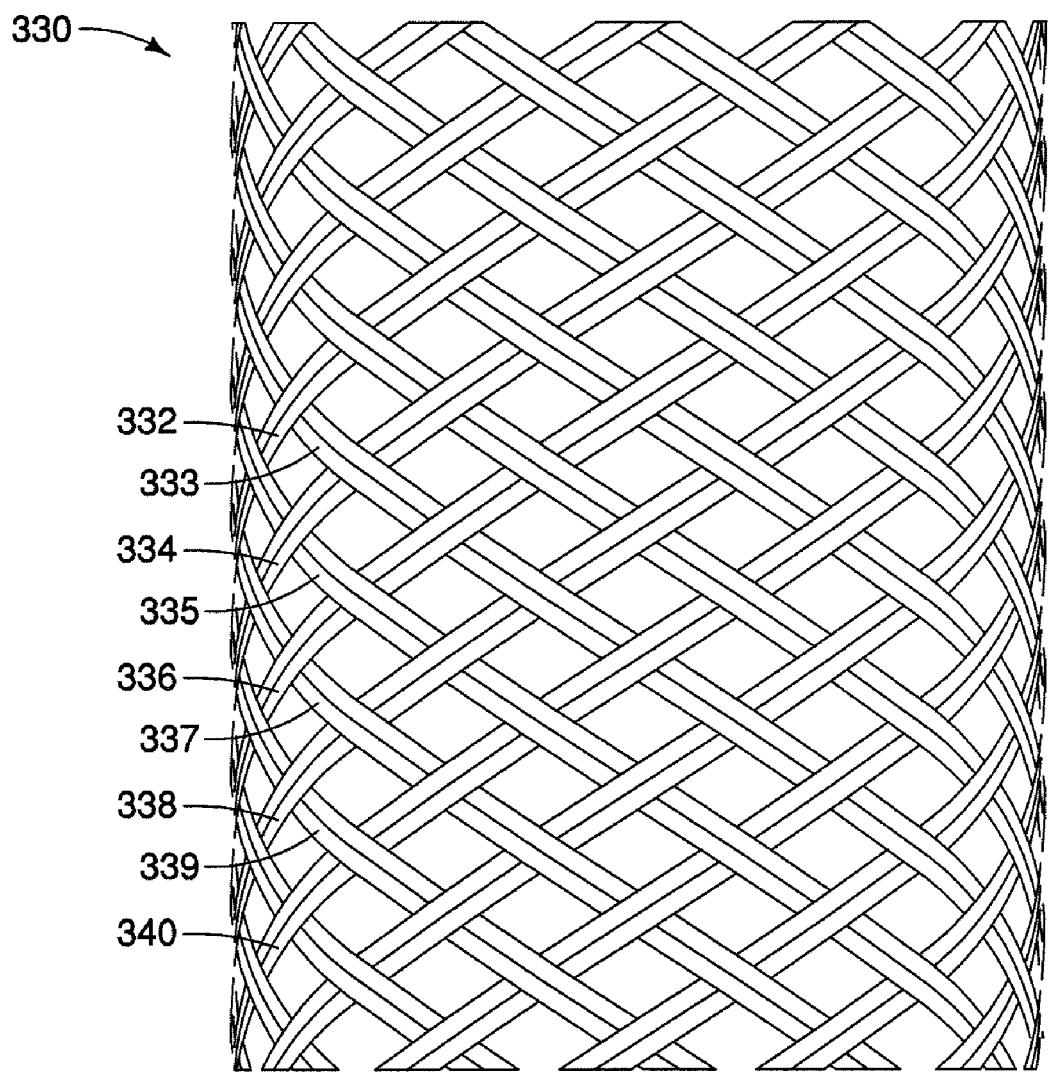
FIG. 6 is a perspective view of a diamond braid pattern in which two conductors travel side-by-side and pass over two side-by-side polymeric strands then under two side-by-side polymeric strands.

FIG. 6 illustrates another braid pattern 330, termed a "diamond pattern, full load." In this pattern, five pairs of conductor strands 332, 334, 336, 338 and 340 pass from the lower left to the upper right. Four pairs of polymeric strands 333, 335, 337 and 339 pass from the lower right to the upper left. Each strand in a pair travels side-by-side in the same phase with its paired strand. In this embodiment, each pair of strands is in one of two phases, which repeat with every other pair of strands. Conductor strand pairs 332 and 334 are both in the same phase with respect to polymeric strand pair 333. In this embodiment, there are the same number of conductor strands and polymeric strands. In other embodiments, this relative number can vary, for example, with one conductor strand pair passing over a single polymeric strand then under a single polymeric strand, rather than a strand pair as shown in FIG. 6.

Figure 7:
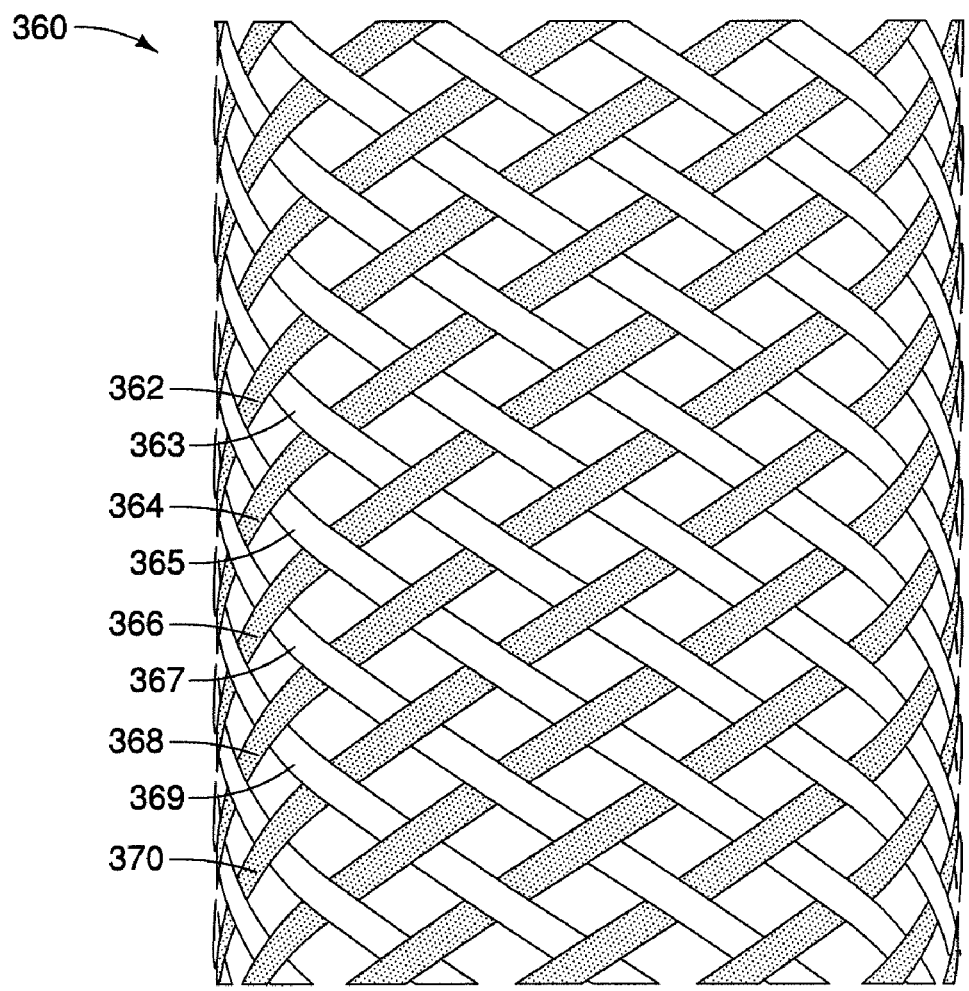
FIG. 7 is a perspective view of a diamond braid pattern in which a conductor passes under one polymeric strand then over one polymeric strand.

FIG. 7 illustrates another braid pattern 360, referred to as a diamond braid pattern. This pattern can also be referred to as a "diamond pattern, half." In this pattern, a conductor strand passes under one polymeric strand then over one polymeric strand. As shown, conductor strands 362, 364, 366, 368 and 370 pass from the lower left to the upper right while polymeric strands 363, 365, 367 and 369 pass from the lower right to the upper left. In this example, the strands are in one of two phases with adjacent strands being out of phase with respect to each other.

Figure 8:
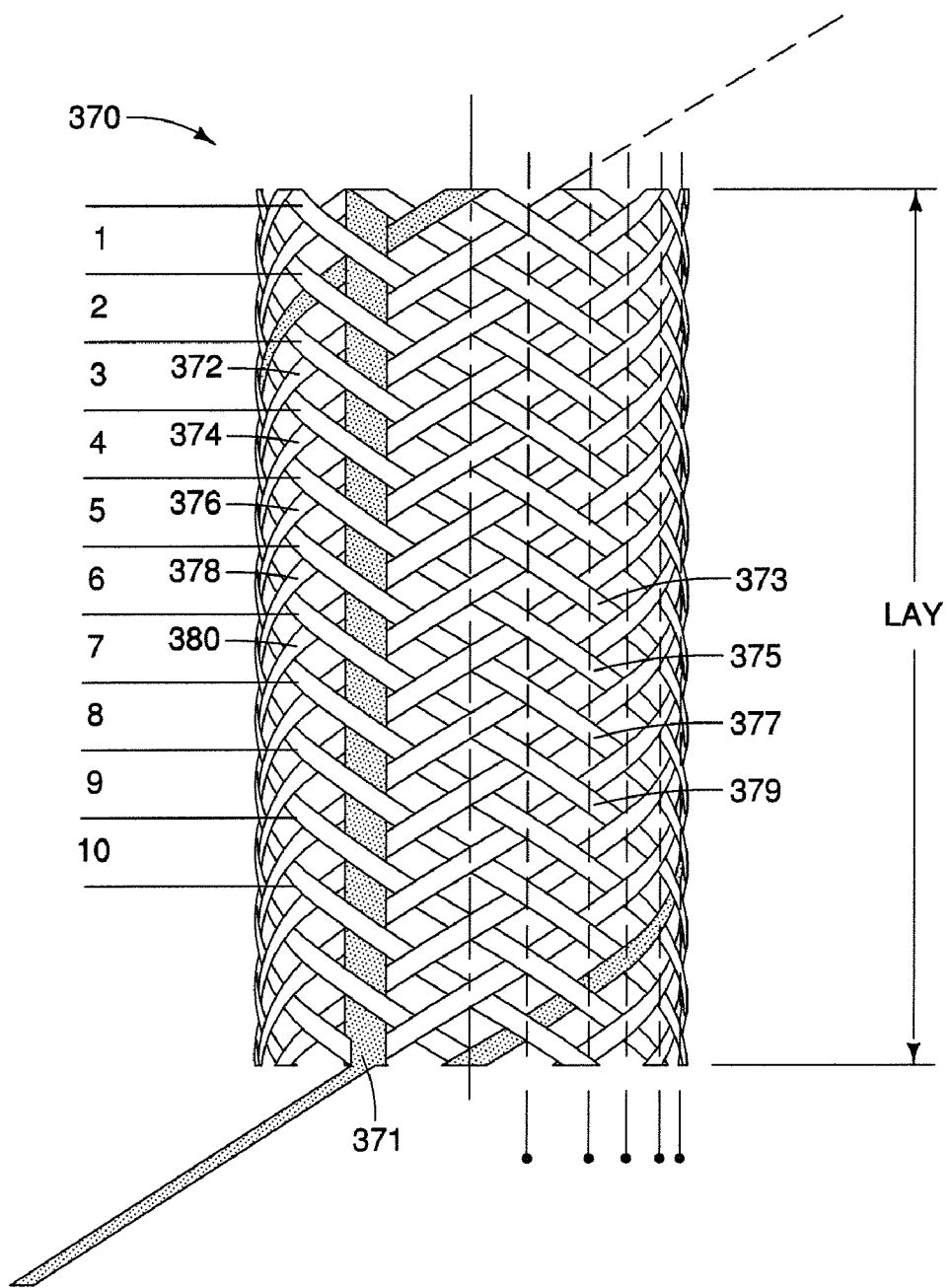
FIG. 8 is a perspective view of a regular braid pattern having an additional zero degree conductor strand.

FIG. 8 illustrates another braid pattern 370 having strands 372, 374, 376, 378 and 380 passing from the lower left to the upper right. Strands 373, 375, 377 and 379 pass from the lower right to the upper left, each strand passing over two then under two. An additional strand 371 is shown, which can be a conductor strand termed a triaxial fiber, a warp fiber, or a zero degree fiber. In some embodiments, the strands in the braid are polymeric strands and the zero degree strand is a conductor strand. In some embodiments, there is more than one zero degree conductor strand disposed about the braid, for example 2, 3, 4 or more zero degree conductor strands.

In the braided embodiments, the braid maintains the spacing from one conductor to another. In some embodiments, the braiding is performed over a mandrel, for example, a TEFLON® coated mandrel. Tubing can be placed over the braid. The tubing and polymer may be formed of the same or similar materials, for example, a thermoplastic polymeric material. The tubing having the braided polymer and insulated conductor strands within can be placed in a heat shrink tubing or other structure and a reflow operation performed. The polymer strands and the outer tubing can become one, which may reduce the profile of the lead body.

In some embodiments of the invention, the conductors and polymer strands are braided over a mandrel and the mandrel later removed, sometimes after further joining the insulated conductors and polymer strands with a reflow step. A lumen may remain in such embodiments. In other embodiments, the strands are braided over a solid shaft, for example, a polymer or metal shaft, which remains after the braiding and any reflow. In still another embodiment, the strands are braided over a tube having a lumen, which may remain after any reflow step to provide a lumen.

The polymer strands may be formed of a biocompatible material, for example, polyester. Some polymer strands are round and have about a 0.005 inch O.D., while the insulated conductors have about a 0.006 inch O.D. and include seven filaments.

It is appreciated that various modifications to the inventive concepts described herein may be apparent to those of ordinary skill in the art without departing from the scope of the present invention as defined by the appended claims.

What is claimed is:

1. An implantable medical lead comprising a multi-conductor cable, the multi-conductor cable consisting of:
   a) a plurality of individually insulated conductor strands that do not cross over each other;
   b) a plurality of at least N polymer strands, where N is at least two; and
   c) wherein the plurality of individually insulated conductor strands are helically wound in a first direction and the plurality of polymer strands are helically wound in a second direction opposite the first.

2. The implantable medical lead of claim 1 wherein the polymer strands and the conductor strands are braided such that the conductor strands pass over two polymer strands then under two polymer strands in a repeating manner.

3. The implantable medical lead of claim 1 wherein the number of polymer strands is at least equal to the number of insulated conductor strands.

4. The implantable medical lead of claim 1 having an outer diameter of less than about 4 mm.

5. The implantable medical lead of claim 1 wherein the insulated conductors have an outer diameter of less than about ¼ mm.

6. The implantable medical lead of claim 1 having a length from about 5 cm to about 150 cm.

7. The implantable medical lead of claim 1 wherein N is equal to at least 4.

8. The implantable medical lead of claim 1 comprising a first set of electrodes disposed in the first end region.

9. The implantable medical lead of claim 8 comprising a second set of electrical contacts disposed in the second end region.

10. The implantable medical lead of claim 8 wherein the second end region is adapted for connection to a lead extension.

11. The implantable medical lead of claim 1 including a tubular sidewall housing the multi-conductor-cable, the tubular sidewall comprising an outer jacket disposed around the individually insulated conductor strands and the polymer strands.

12. The implantable medical lead of claim 1 including a stylet entrance.

13. The implantable medical lead of claim 12 wherein the stylet entrance is about 20 cm to 50 cm from a distal end of the lead.

14. An implantable medical lead, comprising:
   a) a multi-conductor cable;
   b) a tubular sidewall having a length extending between and to a first end region and a second end region opposite the first end region, wherein the tubular sidewall houses the multi-conductor cable, the multi-conductor cable consisting of:
      i) a plurality of insulated conductor strands that do not cross over each other;
      ii) a plurality of at least N polymer strands, where N is at least two; and
      iii) wherein the plurality of insulated conductor strands are helically wound in a first direction and the plurality of polymer strands are helically wound in a second direction opposite the first;
   c) at least one first electrode electrically connected to at least one of the insulated conductor strands in the first end region of the lead body; and
   d) at least one second electrical contact connected to the at least one insulated conductor strand in the second region of the lead body, opposite the first electrode,
   e) wherein the first electrode is contactable with living body tissue and the second electrical contact is connectable to an implantable pulse generator device.

15. The implantable medical lead of claim 14 wherein the polymer strands and the conductor strands are braided such that the conductor strands pass over two polymer strands then. under two polymer ands in a repeating manner.

16. The implantable medical lead of claim 14 wherein the number of polymer strands is at least equal to the number of insulated conductor strands.

17. The implantable medical lead of claim 14 comprising an outer diameter of less than about 4 mm.

18. The implantable medical lead of claim 14 wherein the insulated conductors have an outer diameter of less than about ¼ mm.

19. The implantable medical lead of claim 14 having a length from about 5 cm to about 150 cm.

20. The implantable medical lead of claim 14 wherein N is equal to at least 4.

21. The implantable medical lead of claim 14 comprising a first set of electrodes disposed in the first end region.

22. The implantable medical lead of claim 21 comprising a second set of electrical contacts disposed in the second end region.

23. The implantable medical lead of claim 21 wherein the second end region is adapted for connection to a lead extension.

24. The implantable medical lead of claim 14 wherein the tubular sidewall comprises an outer jacket disposed around the insulated conductor strands and the polymer strands.

25. The implantable medical lead of claim 14 including a stylet entrance.

26. The implantable medical lead of claim 25 wherein the stylet entrance is about 20 cm to 50 cm from a distal end of the lead.

* * * * *

UNITED STATES PATENT AND TRADEMARK OFFICE
CERTIFICATE OF CORRECTION

| | | |
|---|---|---|
| PATENT NO. | : 8,160,719 B2 | Page 1 of 1 |
| APPLICATION NO. | : 11/959730 | |
| DATED | : April 17, 2012 | |
| INVENTOR(S) | : Swoyer et al | |

It is certified that error appears in the above-identified patent and that said Letters Patent is hereby corrected as shown below:

Column 8, line 27 delete "ands" and insert --strands--

Signed and Sealed this
Twelfth Day of June, 2012

David J. Kappos
*Director of the United States Patent and Trademark Office*